US010846047B2

(12) United States Patent
Pitera

(10) Patent No.: US 10,846,047 B2
(45) Date of Patent: Nov. 24, 2020

(54) PORTABLE AUDIO DEVICE FOR FACILITATING GUIDED MINDFULNESS MEDITATION SESSIONS

(71) Applicant: Rootinely, LLC, Dana Point, CA (US)

(72) Inventor: Robert Pitera, Dana Pont, CA (US)

(73) Assignee: ROOTINELY, LLC, Dana Point, CA (US)

( * ) Notice: Subject to any disclaimer, the term of this patent is extended or adjusted under 35 U.S.C. 154(b) by 305 days.

(21) Appl. No.: 16/006,455

(22) Filed: Jun. 12, 2018

(65) Prior Publication Data
US 2018/0364968 A1     Dec. 20, 2018

Related U.S. Application Data

(60) Provisional application No. 62/520,388, filed on Jun. 15, 2017.

(51) Int. Cl.
| | |
|---|---|
| *A61M 21/02* | (2006.01) |
| *G06F 3/16* | (2006.01) |
| *H04R 1/02* | (2006.01) |
| *A61M 21/00* | (2006.01) |

(52) U.S. Cl.
CPC ............. *G06F 3/165* (2013.01); *A61M 21/02* (2013.01); *H04R 1/025* (2013.01); *A61M 2021/0027* (2013.01); *A61M 2205/3553* (2013.01); *A61M 2205/3584* (2013.01); *A61M 2205/3592* (2013.01); *H04R 1/028* (2013.01); *H04R 2420/07* (2013.01); *H04R 2499/11* (2013.01)

(58) Field of Classification Search
CPC ............................... A61M 21/00; A61M 21/02
USPC ...................................... 600/26–28
See application file for complete search history.

(56) References Cited

U.S. PATENT DOCUMENTS

| | | | |
|---|---|---|---|
| 2016/0151603 A1* | 6/2016 | Shouldice | A61B 5/486 600/28 |
| 2020/0001040 A1* | 1/2020 | Gloria | A61B 5/6891 |
| 2020/0069966 A1* | 3/2020 | Porter | H04R 5/033 |

\* cited by examiner

*Primary Examiner* — John P Lacyk
(74) *Attorney, Agent, or Firm* — Hankin Patent Law, APC; Kevin Schraven; Anooj Patel

(57) ABSTRACT

The present disclosure is directed to a portable audio device that allows a user to easily access guided meditation sessions stored thereon to promote regular meditation practice. The portable audio device minimizes user effort with a goal to improve adoption of mindfulness meditation practice. In one embodiment, the portable audio device may be programmed to play guided mindfulness meditation sessions. In one embodiment, the portable audio device may include meditation modules that have predefined themes, and serve as a prompt or reminder for regular meditation practice.

17 Claims, 4 Drawing Sheets

PORTABLE AUDIO DEVICE FOR FACILITATING GUIDED MINDFULNESS MEDITATION SESSIONS

CROSS-REFERENCE TO RELATED APPLICATION

This application claims the benefit of U.S. Provisional Application No. 62/520,388, filed on Jun. 15, 2017, entitled "A Counter-Top Speaker Device that Plays Random Generated Mindfulness Meditation Sessions", the contents of which are incorporated herein by reference as though set forth in their entirety.

BACKGROUND

The present disclosure is directed to an audio device for facilitating guided meditation practice, and more particularly, to a counter-top or portable audio device that is programmed to play guided mindfulness meditation sessions within predefined themes.

Mindful meditation practice is typically perceived as complex and time consuming for many individuals. That is unfortunate, since the benefits of mindful meditation are great, even for those individuals who can only engage in mindful meditation on a limited basis. Yet many individuals find it difficult to integrate meditation into a daily routine. This is problem for such individuals, as well as children, and for the practice of meditation to grow.

Currently, there are a number of options and/or devices that address the difficulties of integrating mindful meditation practice into a daily routine. Ironically, however, these existing options tend to increase the demands placed on users, often requiring increased user interaction to operate. Furthermore, some of the existing options are based on smart phone or table computing device applications, which offer the benefit of mobility to busy individuals. Nevertheless, even the mobile device-based options have limitations. Typically, a mindful meditation application is downloaded onto a user's mobile device, and the user accesses the application via the mobile device. Often, the user will engage in meditation at night, and the use of mobile devices at night may impact the sleep and health of the user. Mobile computing devices and the applications operating thereon often create distractions for the user, particularly children, interfering with the meditation session. In addition, many locations, such as schools, restrict access to mobile computing devices Therefore, there is a need for a portable audio device that allows a user to easily access guided meditation sessions stored thereon to promote regular meditation practice.

SUMMARY

The following presents a simplified overview of the example embodiments in order to provide a basic understanding of some embodiments of the example embodiments. This overview is not an extensive overview of the example embodiments. It is intended to neither identify key or critical elements of the example embodiments nor delineate the scope of the appended claims. Its sole purpose is to present some concepts of the example embodiments in a simplified form as a prelude to the more detailed description that is presented hereinbelow. It is to be understood that both the following general description and the following detailed description are exemplary and explanatory only and are not restrictive.

In accordance with the embodiments disclosed herein, the present disclosure is directed to a portable audio device that allows a user to easily access guided meditation sessions stored thereon to promote regular meditation practice. The portable audio device minimizes user effort with a goal to improve adoption of mindfulness meditation practice. The portable audio device for facilitating guided meditation session may be implemented at a reasonable cost making the benefits of guided meditation available to the average consumer.

In accordance with one embodiment of the present disclosure, there is provided a portable audio device for facilitating guided meditation sessions. The portable audio device comprises a device processor operable for controlling the portable audio device; an input/output device operatively connected to the device processor and controlled in part by the device processor, wherein the input/output device is operable to transmit data to and from the device processor; an audio output component operatively coupled to the device processor and controlled in part by the device processor, wherein the audio output component is operable to output a plurality of sounds therefrom; and a power source operatively coupled to the device processor, wherein the power source is operable to generate a supply of power for operation of the portable audio device.

The audio output component comprises an audio memory operable to store an audio library comprising a plurality of audio data files containing audio data for playback thereof, wherein the plurality of audio data files comprises a plurality of guided meditation programs, wherein the plurality of guided meditation programs include a plurality of guided meditation program modes. The audio output component further comprises an audio controller operable to access audio data contained in at least one of the plurality of audio data files, wherein the audio controller is operable to generate, based on at least a portion of the accessed audio data, at least one audio output control signal for controlling the output of a guided meditation program. The audio output component also includes a speaker component operatively coupled to the audio controller and controlled in part by the audio controller, wherein the speaker component is operable to output the guided meditation program in accordance with the at least one audio output control signal.

The device processor of the portable audio device is operable to obtain data associated with at least one operational parameter for an audio output of a guided meditation program by the audio output component. The device processor generates at least one device control signal for controlling the at least one operational parameter for the audio output of the guided meditation program and transmits the at least one device control signal to the audio output component for outputting the at least one guided meditation program in accordance with the at least one device control signal.

In one embodiment, the at least one operational parameter for an audio output of a guided meditation program by the audio output component is selected from the group consisting of a selection of at least one guided meditation program to be output, an audio characteristic of a guided meditation program to be output, a timing of a guided meditation program to be output, a duration of a guided meditation program to be output, and combinations thereof.

In one embodiment, the audio controller is operable to generate, based on at least a portion of the accessed audio data, at least one audio output control signal for controlling at least one of: a type of guided meditation program output from the audio output component, an audio characteristic of a guided meditation program emitted from the audio output component, a timing of a guided meditation program emitted from the audio output component, and combinations thereof.

In one embodiment, at least portion of the plurality of guided meditation programs have a duration of less than 10 minutes. In a preferred embodiment, the plurality of guided meditation program modes comprises a least a short duration program mode and a long duration program mode. In a more preferred embodiment, the short duration program mode has a duration of approximately 2 minutes to approximately 5 minutes and wherein the long duration program mode has a duration of approximately 5 minutes to approximately 10 minutes.

In one embodiment, the plurality of guided mediation program modes comprises a plurality of predefined theme modes, wherein each predefined theme mode comprises guided meditation programs containing content directed to the predefined theme. In a preferred embodiment, the predefined theme modes are selected from the group consisting of breath, heart, performance, body scan, and stress and anxiety.

In another embodiment, the input/output device is operable to receive a plurality of commands for controlling at least one operational parameter for an audio output of a guided meditation program by the audio output component. In a preferred embodiment, the input/output device further comprises a user interface, wherein at least a portion of the plurality of commands are received from an associated user via the user interface.

In another embodiment, the input/output device is operable to connect the device processor to an associated network for communication with a remote computing device, wherein the input/output device is operable to receive data from the remote computing device and transmit the received data to the device processor for processing thereof. In a preferred embodiment, the input/output device is operable to receive a plurality of commands from the remote computing device for controlling at least one operational parameter for an audio output of a guided meditation program by the audio output component.

In accordance with one embodiment of the present disclosure, there is provided a method for facilitating guided meditation sessions via a portable audio device. The portable audio device comprises a device processor operable controlling the portable audio device, an input/output device is operable to transmit data to and from the device processor, an audio output component is operable to output a plurality of sounds therefrom, and a power source operable to generate a supply of power for operation of the portable audio device. The audio output component comprises an audio memory operable to store an audio library comprising a plurality of audio data files containing audio data for playback thereof, wherein the plurality of audio data files comprises a plurality of guided meditation programs, wherein the plurality of guided meditation programs includes a plurality of guided meditation program modes. The audio output component further comprises an audio controller operable to access audio data contained in at least one of the plurality of audio data files, and a speaker component operable to output guided meditation programs.

The method comprises receiving a command to activate the portable audio device. The device processor obtains data associated with at least one operational parameter for an audio output of a guided meditation program and generates at least one device control signal for controlling the at least one operational parameter for the audio output of the guided meditation program. The input/output device transmits the at least one device control signal to the audio controller. The audio controller accesses audio data contained in at least one of the plurality of audio data files in accordance with at least one device control signal. Based on at least a portion of the accessed audio data, the audio controller generates at least one audio output control signal for controlling the output of a guided meditation program. The speaker component outputs the guided meditation program in accordance with the at least one audio output control signal.

In one embodiment, the at least one operational parameter for an audio output of a guided meditation program by the audio output component is selected from the group consisting of a selection of at least one guided meditation program to be output, an audio characteristic of a guided meditation program to be output, a timing of a guided meditation program to be output, a duration of a guided meditation program to be output, and combinations thereof.

In one embodiment, at least portion of the plurality of guided meditation programs have a duration of less than 10 minutes. In a preferred embodiment, the plurality of guided meditation program modes comprises a least a short duration program mode and a long duration program mode. In a more preferred embodiment, the short duration program mode has a duration of approximately 2 minutes to approximately 5 minutes and wherein the long duration program mode has a duration of approximately 5 minutes to approximately 10 minutes.

In one embodiment, the plurality of guided mediation program modes comprises a plurality of predefined theme modes, wherein each predefined theme mode comprises guided meditation programs containing content directed to the predefined theme.

In another embodiment, the method further comprises receiving, via the input/output device, a plurality of commands for controlling at least one operational parameter for an audio output of a guided meditation program by the audio output component. In one embodiment, the method further comprises receiving, via the input/output device, data from a remote computing device via an associated network and transmitting the received data to the device processor for processing thereof.

Still other advantages, embodiments, and features of the subject disclosure will become readily apparent to those of ordinary skill in the art from the following description wherein there is shown and described a preferred embodiment of the present disclosure, simply by way of illustration of one of the best modes best suited to carry out the subject disclosure. As it will be realized, the present disclosure is capable of other different embodiments and its several details are capable of modifications in various obvious embodiments all without departing from, or limiting, the scope herein. Accordingly, the drawings and descriptions will be regarded as illustrative in nature and not as restrictive.

BRIEF DESCRIPTION OF THE DRAWINGS

The drawings are of illustrative embodiments. They do not illustrate all embodiments. Other embodiments may be used in addition or instead. Details which may be apparent or unnecessary may be omitted to save space or for more effective illustration. Some embodiments may be practiced with additional components or steps and/or without all of the components or steps which are illustrated. When the same numeral appears in different drawings, it refers to the same or like components or steps.

DETAILED DESCRIPTION OF THE ILLUSTRATIVE EMBODIMENTS

Figure 1:
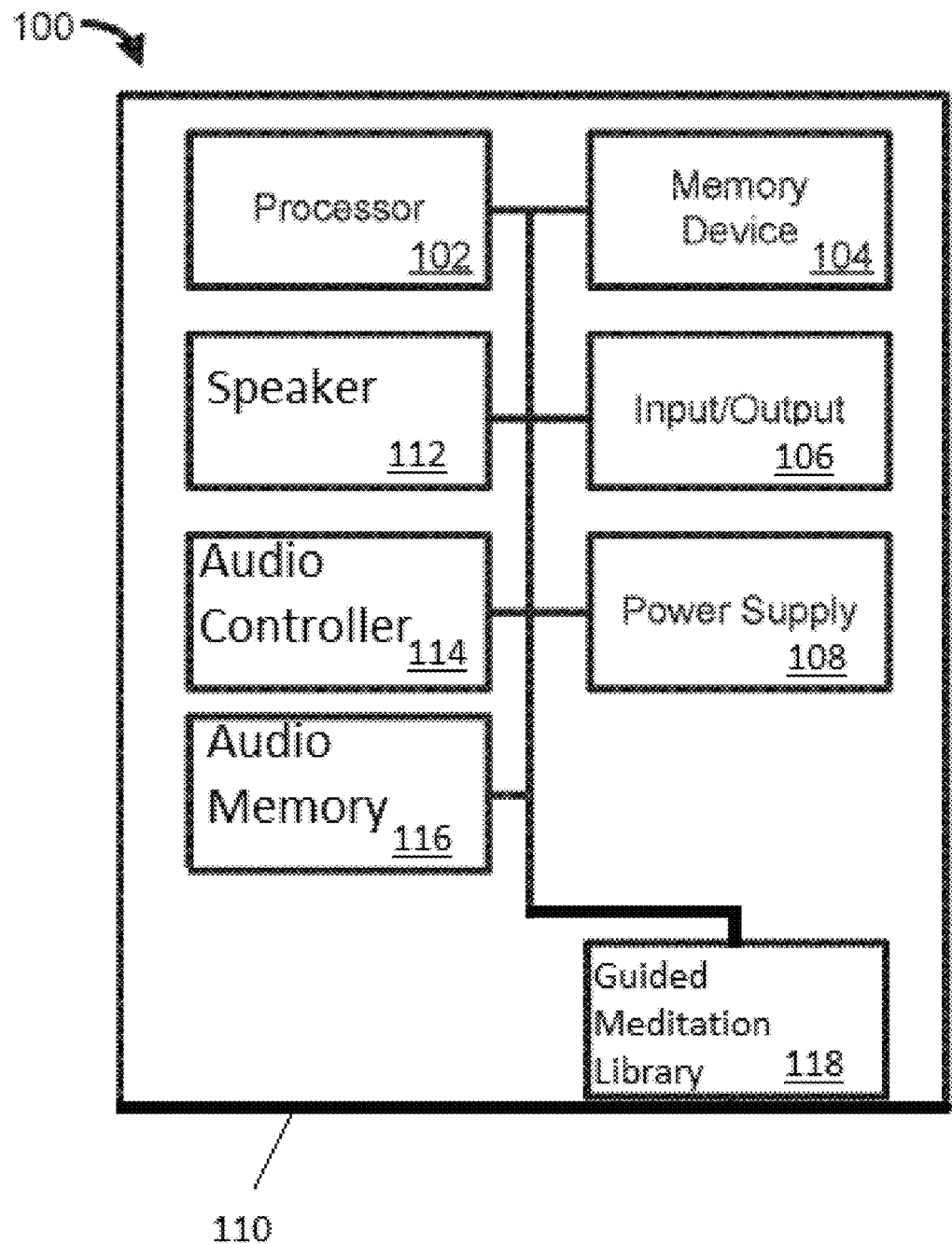
FIG. 1 is a schematic diagram illustrating an example embodiment of a portable audio device for facilitating guided meditation sessions according to the present disclosure.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are signify both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that may be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all embodiments of this application including, but not limited to, steps in disclosed methods. Thus, if there are a variety of additional steps that may be performed it is understood that each of these additional steps may be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware embodiments. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, may be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that may direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, may be implemented by special purpose hardware-based computer systems that perform the specified functions or steps, or combinations of special purpose hardware and computer instructions.

In the following description, certain terminology is used to describe certain features of one or more embodiments. For purposes of the specification, unless otherwise specified, the term "substantially" refers to the complete or nearly complete extent or degree of an action, characteristic, property, state, structure, item, or result. For example, in one embodiment, an object that is "substantially" located within a housing would mean that the object is either completely within a housing or nearly completely within a housing. The exact allowable degree of deviation from absolute completeness may in some cases depend on the specific context.

However, generally speaking, the nearness of completion will be so as to have the same overall result as if absolute and total completion were obtained. The use of "substantially" is also equally applicable when used in a negative connotation to refer to the complete or near complete lack of an action, characteristic, property, state, structure, item, or result.

As used herein, the terms "approximately" and "about" generally refer to a deviance of within 5% of the indicated number or range of numbers. In one embodiment, the term "approximately" and "about", may refer to a deviance of between 0.001-10% from the indicated number or range of numbers.

Various embodiments are now described with reference to the drawings. In the following description, for purposes of explanation, numerous specific details are set forth in order to provide a thorough understanding of one or more embodiments. It may be evident, however, that the various embodiments may be practiced without these specific details. In other instances, well-known structures and devices are shown in block diagram form to facilitate describing these embodiments.

In various implementations, there may be provided a portable audio device that allows a user to easily access guided meditation sessions stored thereon to promote regular meditation practice. The portable audio device minimizes user effort with a goal to improve adoption of mindfulness meditation practice. In one embodiment, the portable audio device may be programmed to play guided mindfulness meditation sessions. In one embodiment, the portable audio device may include meditation modules having predefined themes, and serve as a prompt or reminder for regular meditation practice.

FIG. 1 is a high-level block diagram illustrating of a portable audio device 100 according to the present disclosure. The portable audio device 100 may comprise any suitable housing 110 for enclosing and protecting the various components disclosed herein. The portable audio device 100 may comprise a processor 102 operable to control the operation of the portable audio device 100. The processor 102 may be, or may comprise, any suitable microprocessor or microcontroller, for example, a low-power application-specific controller (ASIC) and/or a field programmable gate array (FPGA) designed or programmed specifically for the task of controlling a device as described herein, or a general purpose central processing unit (CPU), for example, one based on 80×86 architecture as designed by Intel™ or AMD™, or a system-on-a-chip as designed by ARM™. The processor 102 may be coupled (e.g., communicatively, operatively, etc.) to auxiliary devices or modules of the portable audio device 100 using a bus or other coupling as is known in the art. The electronic vaporizing device 100 may comprise a power supply 108. The power supply 108 may comprise one or more batteries and/or other power storage device (e.g., capacitor) and/or a port for connecting to an external power supply. The one or more batteries may be rechargeable. The one or more batteries may comprise a lithium-ion battery (including thin film lithium ion batteries), a lithium-ion polymer battery, a nickel-cadmium battery, a nickel metal hydride battery, a lead-acid battery, combinations thereof, and the like. For example, an external power supply may supply power to the portable audio device 100 and a battery may store at least a portion of the supplied power.

The electronic vaporizing device 100 may comprise a memory device 104 coupled to the processor 102. The memory device 104 may comprise a random-access memory (RAM) configured for storing program instructions and data for execution or processing by the processor 102 during control of the portable audio device 100. When the portable audio device 100 is powered off or in an inactive state, program instructions and data may be stored in a long-term memory, for example, a non-volatile magnetic optical, or electronic memory storage device (not shown). At least one of the RAM or the long-term memory may comprise a non-transitory, computer-readable medium storing program instructions that, when executed by the processor 102, cause the portable audio device 100 to perform all or part of one or more methods and/or operations described herein. Program instructions may be written in any suitable high-level language, for example, C, C++, C# or the Java™, and compiled to produce machine-language code for execution by the processor 102.

In an embodiment, the portable audio device 100 may also comprise an input/output device 106 coupled to the processor 102. Input may be received from a user or another device and/or output may be provided to a user or another device via the input/output device 106. The input/output device 106 may comprise any combinations of input and/or output devices such as buttons, knobs, keyboards, touchscreens, displays, light-emitting elements, a speaker, and/or the like. In an embodiment, the input/output device 106 may comprise an interface port (not shown) such as a wired interface, for example a serial port, a Universal Serial Bus (USB) port, an Ethernet port, or other suitable wired connection. The input/output device 106 may comprise a wireless interface (not shown), for example a transceiver using any suitable wireless protocol, for example WiFi (IEEE 802.11), Bluetooth®, infrared, or other wireless standard. For example, the input/output device 106 may communicate with a smartphone via Bluetooth® such that the inputs and outputs of the smartphone may be used by the user to interface with the electronic vaporizing device 100. In an embodiment, the input/output device 106 may comprise a user interface. The user interface user interface may comprise at least one of lighted signal lights, gauges, boxes, forms, check marks, avatars, visual images, graphic designs, lists, active calibrations or calculations, 2D interactive fractal designs, 3D fractal designs, 2D and/or 3D representations, and other interface system functions.

In an embodiment, the input/output device 106 may comprise a touchscreen interface and/or a biometric interface. For example, the input/output device 106 may include controls that allow the user to interact with and input information and commands to the portable audio device 100. For example, with respect to the embodiments described herein, the input/output device 106 may comprise a touch screen display. The input/output device 106 may be configured to provide selected content, which are presented to the user via the functionality of a display. User inputs to the touch screen display are processed by, for example, the input/output device 106 and/or the processor 102. The input/output device 106 may also be configured to process new content and communications to the portable audio device 100. The touch screen display may provide controls and menu selections, and process commands and requests. Application and content objects may be provided by the touch screen display. The input/output device 106 and/or the processor 102 may receive and interpret commands and other inputs, interface with the other components of the portable audio device 100 as required. In an embodiment, the touch screen display may enable a user to lock, unlock, or partially unlock or lock, the portable audio device 100. The portable audio device 100 may be transitioned from an idle and locked state into an open state by, for example, moving or dragging an icon on the screen of the portable audio device 100, entering in a password/passcode, and the like.

The portable audio device 100 may also include a speaker component 112 and an audio controller, or audio chip, 114, capable of causing the speaker component 112 to output a plurality of guided meditation sessions. In some embodiments, the audio controller 114 may be a micro sound chip. In some embodiments, the speaker component 112 may also be designed to output other sounds. In some embodiments, the speaker component 112 may be controlled by the processor 102.

In some embodiments, the audio controller 114 and/or the portable audio device 100 includes an audio memory 116 containing instructions for playing predetermined sounds and/or containing one or more sound files to be output via the speaker component 112. Additionally, or instead, the audio controller 114 may be micro-coded or hard-wired to play predetermined sounds. In some embodiments, the audio controller 114 may cause the speaker component 112 to output sound as it is stored in the memory 104, micro-coded, and/or hard-wired. However, in some embodiments, the processor 102 may instruct/cause the audio controller 114 to output the sound with one or more adjusted characteristics. The characteristics can include, for example, a tone, a volume, a pitch, a number of harmonics, or a frequency of one or more harmonics.

In some embodiments, the memory 104 may include instructions for generating sound and/or sound files, and in some embodiments the processor 102 may be micro-coded and/or hard-wired to play sound files. In that regard, the instructions may be performed by the processor 102 which may directly control the speaker component 112 and/or may instruct the audio controller 114 to control the speaker component to output one or more sounds. In some embodiments, the processor 102 may communicate with another device, such as another device similar to the portable audio device 100, via the input/output device 106.

In one embodiment, the audio memory 116 is configured to store a plurality of guided meditation audio files. In a preferred embodiment, at least a portion of the plurality of guided meditation audio files may be organized and stored in a Guided Meditation Library as shown at 118. The Guided Meditation Library 118 may include guided meditation sessions and/or content for facilitating guided meditation sessions. In one embodiment, the content of the Guided Meditation Library 118 may be provided by any suitable means. In one embodiment, the content of the Guided Meditation Library 118 may be prerecorded or hard-coded onto the audio memory 116. In another embodiment, the content of the Guided Meditation Library 118 may be input and/or uploaded onto the audio memory 116 via the input/output device 106. In a preferred embodiment, a user of the portable audio device 100 may suitably modify, change, or otherwise customize the content of the Guided Meditation Library 118 to suit the meditation needs of the user.

The Guided Meditation Library 118 may include any meditation sessions and/or content suitable for guided meditation practice. For example, the guided meditation session may include content associated with, but are not limited to, breath, heart, performance, body scan, stress and anxiety, and the like. The guided meditation sessions related to breath may focus the user's attention on the user's breath, open an awareness to distraction, and reorient the user thoughts. The breath sessions may include themes such as breath awareness, breath counting, belly breath, and the like. The guided meditation sessions related to the heart may be designed to build self-esteem and capacity for empathy and gratitude, and may include themes such as gratitude, appreciation, loving kindness, and the like. The guided meditation sessions related to performance may teach tools that improve focus, attention, and motivation in ever-day situations as well as higher stress situations. The performance sessions may include themes such as patience, productivity, focus, meditation, and the like. The guided meditation sessions related to body scan may be designed to develop a mindful awareness of bodily sensations and to relieve tensions, and may include themes such as typical body scans, posture, walking, and the like. The guided meditation sessions related to stress and anxiety may foster the ability to self-regulate, cope with and decrease stress, and bring about a calmer state of mind and greater self-awareness. The stress and anxiety sessions may include themes such as observation, noting, labeling, and the like.

The guided meditation sessions may be of any desired length. In a preferred embodiment, at least a portion of the plurality of guided meditation sessions have a duration of 10 minutes or less. In a preferred embodiment, the guided meditation sessions may be grouped into multiple modes depending on the duration of the guided meditation sessions. For example, the guided meditation sessions may be grouped into a shorter mode comprising sessions having a duration of 2 to 5 minutes, and a longer mode comprising sessions having a duration of 5 to 10 minutes. It is to be understood that the guided meditations may be grouped or divided into any suitable number of modes or formats to allow for effective meditation practice.

Figure 2:
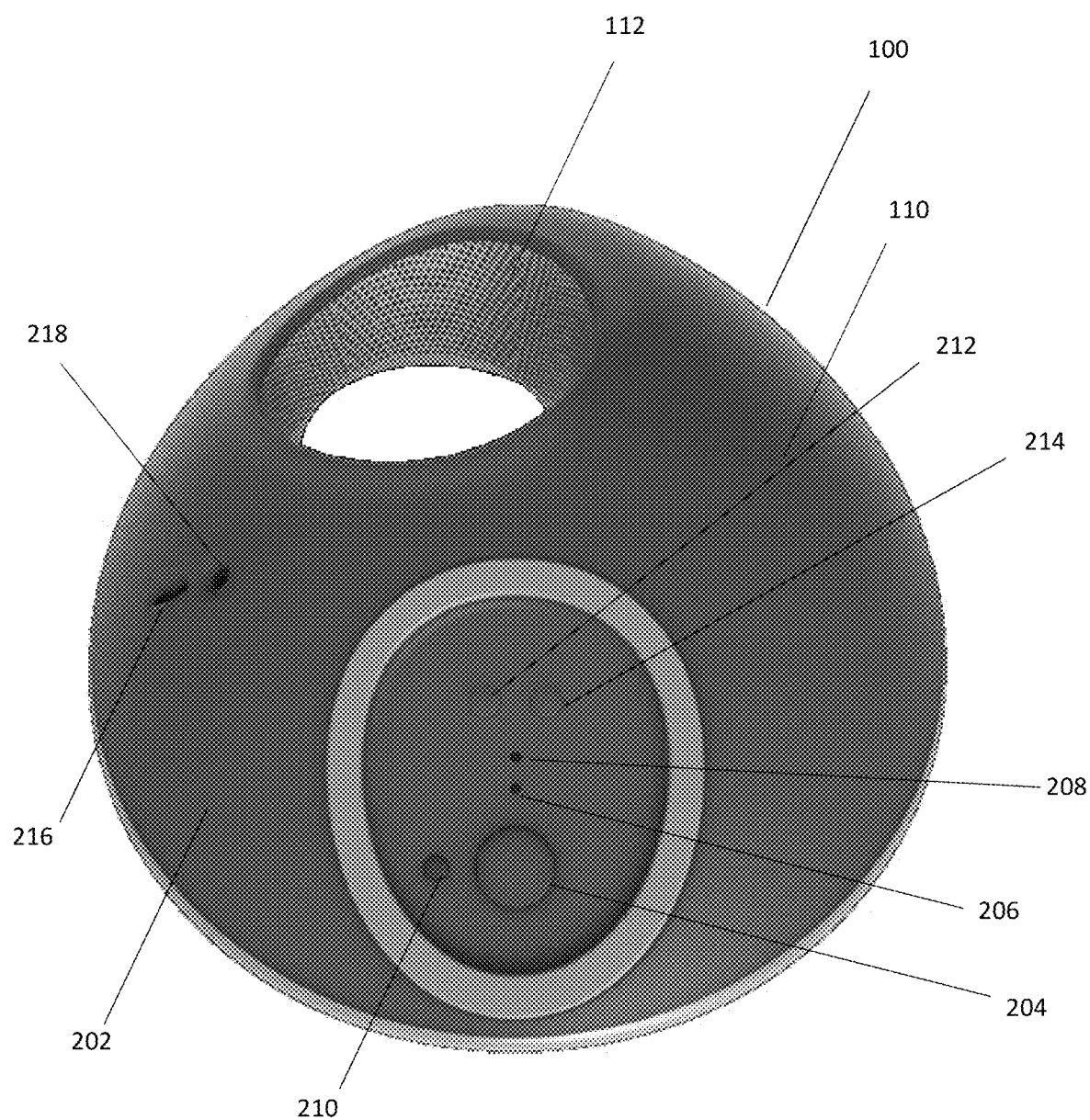
FIG. 2 is an example embodiment of a portable audio device for facilitating guided meditation sessions according to the present disclosure.

FIG. 2 illustrates one embodiment of a portable audio device 100 but illustrates the exterior of the housing 110 and the functionality provided thereon. As shown in FIG. 2, the exterior of the housing 110 includes a front surface 202 which includes operational controls for operation of the portable audio device 100. The front surface 202 may include the speaker component 112 for outputting the plurality of guided meditation sessions.

As FIG. 2 illustrates the front surface 202 may include a power on/off button shown at 204, which allows a user to power on and power off the portable audio device 100. In one embodiment, the power on/off button 204 may also function as a toggle switch, allowing the user to activate other functionalities of the portable audio device 100 by pressing the button repeatedly to control different functions. In one embodiment, the user may press the power on/off button 204 once to power on the portable audio device 100. The user may then press the power on/off button 204 a second time to engage the longer mode of guided meditation sessions. The user may press the power on/off button 204 a third time to engage the shorter mode of guided meditation sessions. As shown at 206 and 208, indicator lights, such as an LED, designate whether the user has selected the longer mode or the short mode.

The front surface 202 may further include an introduction button 210, which when activated by a user of the portable audio device 100 will cause the processor 102 and/or the audio controller 114 to instruct the speaker component to output a guided meditation session. As illustrated in FIG. 2, the front surface may further include a volume up button 212 and a volume down button 214 for controlling the volume of the sound output by the speaker component 112.

In one embodiment, the front surface 202 may also include a micro USB input 216. The micro USB input 216 may provide a connection between an external power supply and the portable audio device 100. In one embodiment, when an external power supply is connected to the micro USB input 216, the external power supply may supply power directly to the portable audio device 100 or may recharge an internal power supply. The micro USB input 216 may also function as an interface port to connect the processor 102 to an auxiliary device or network for the exchange of data therebetween. For example, the micro USB input 216 may be used to connect the processor 102 to an associated network or device to update the program instructions or firmware used in the operation of the portable audio device 100. In another example, the micro USB input 216 may be used to connect the processor 102, memory 104, and/or audio memory 116 to an associated network or device to update, add or modify the content of the Guided Meditation Library 118. It is understood that the processor 102, memory 104, and/or audio memory 116 may connect to an auxiliary device or network for the exchange of data therebetween a wireless interface (not shown), for example a transceiver using any suitable wireless protocol, for example WiFi (IEEE 802.11), Bluetooth®, infrared, or other wireless standard as discussed with respect to FIG. 1.

The portable audio device 100 may also include an auxiliary input 218 on the front surface 202. The auxiliary input 218 may function to connect the processor 102 and/or the audio controller 114 to an auxiliary audio output device, such as external speakers, headphones, and the like. In one embodiment, when an auxiliary audio output device is connected to the auxiliary input 218, the processor 102 and/or audio controller 114 will cause the guided meditation sessions to be output via the auxiliary audio output device. In one embodiment, when an auxiliary audio output device is connected to the auxiliary input 218, the guided meditation sessions will not be output via the speaker component 112.

Figure 3:
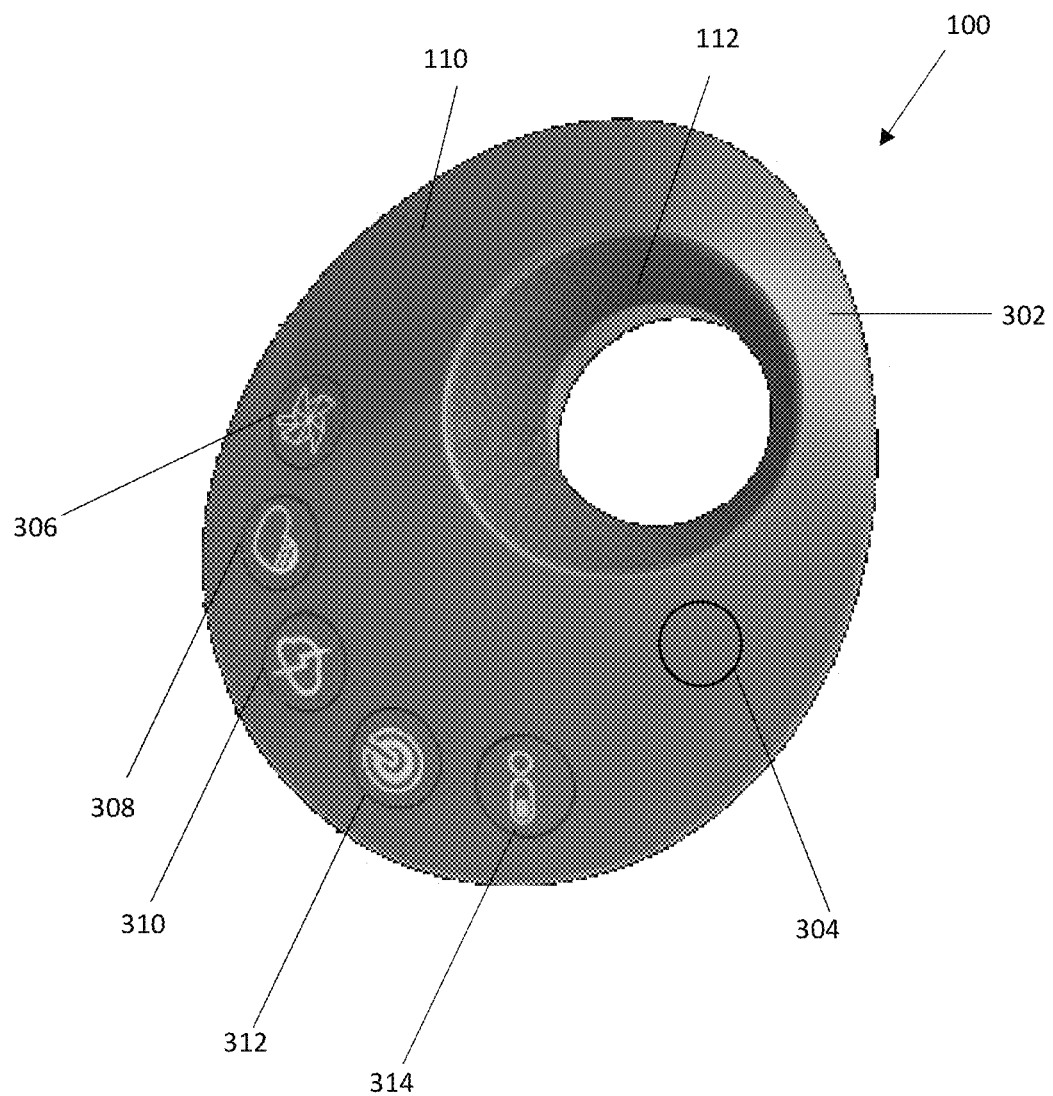
FIG. 3 is another example embodiment of a portable audio device for facilitating guided meditation sessions according to the present disclosure.

FIG. 3 illustrates one embodiment of a portable audio device 100 but illustrates the exterior of the housing 110 and the functionality provided thereon. As shown in FIG. 3, the exterior of the housing 110 includes a front surface 302 which includes operational controls for operation of the portable audio device 100. The front surface 302 may include the speaker component 112 for outputting the plurality of guided meditation sessions.

As FIG. 3 illustrates the front surface 302 may include a power on/off button shown at 304, which allows a user to power on and power off the portable audio device 100. In one embodiment, the power on/off button 304 may also function as a toggle switch, allowing the user to activate other functionalities of the portable audio device 100 by pressing the button repeatedly to control different functions. (Is there an on/off switch? Does it control other functions?)

As shown in FIG. 3, the portable audio device 100 may provide the functionality to allow the user to select guided meditation sessions directed to specific content or theme. In one embodiment, the front surface 302 of the portable audio device 100 may include content selection buttons which allow the user to select a particular content for a guided meditation session. As illustrated in FIG. 3, the user may select meditation sessions directed to breath 306, heart 308, performance 310, body scan 312, and stress and anxiety 314. For example, if the user desires a guided meditation session directed to breath, the user would activate the breath selection button 306. Activation of breath selection button 306 by the user will cause the processor 102 and/or the audio controller 114 to instruct the speaker component to output a guided meditation session directed to breath themes. It is to be understood that the content selection buttons illustrated in FIG. 3 are only examples, and the portable audio device 100 may include any number of content selection buttons and associated content with respect thereto.

Figure 4:
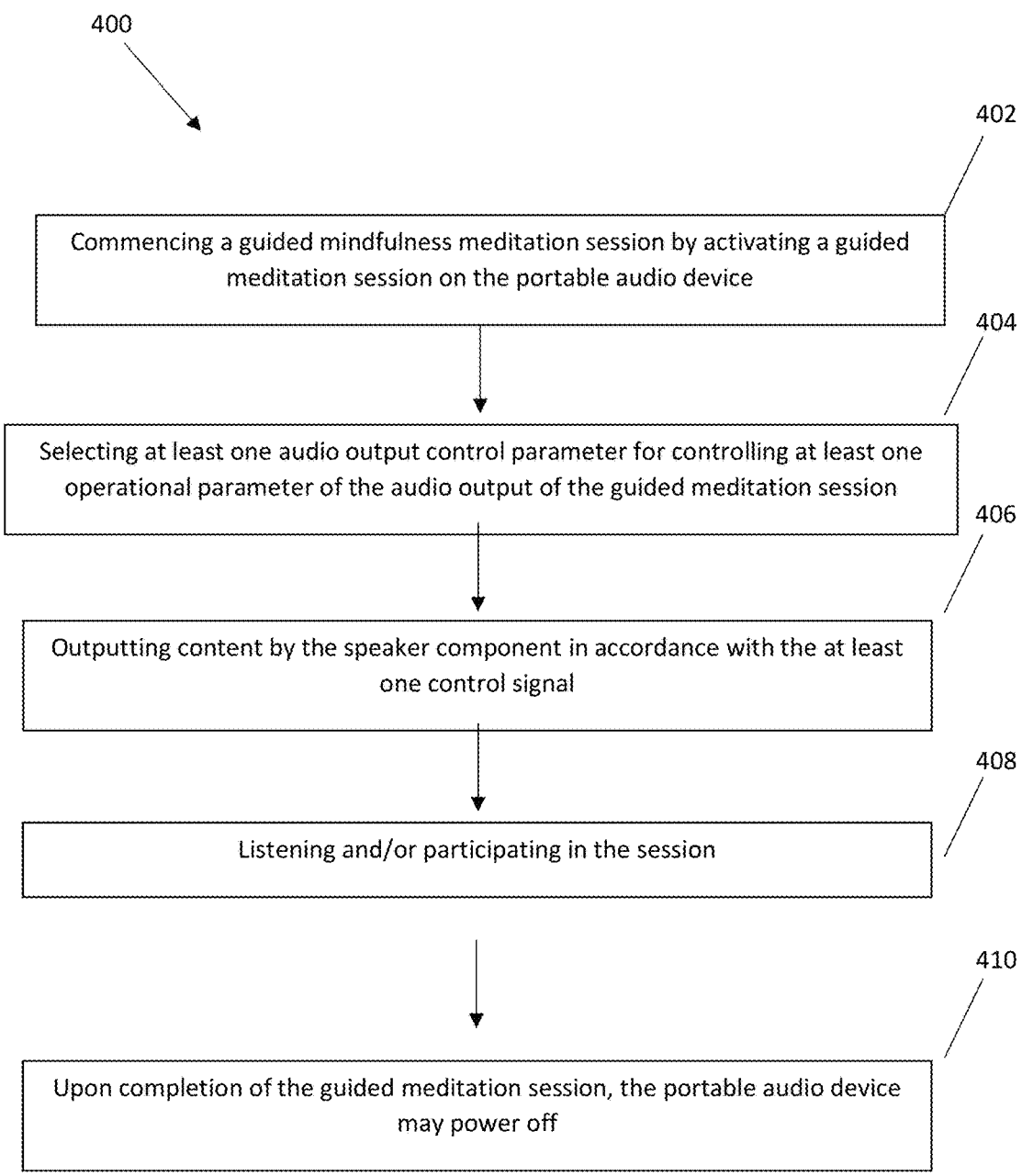
FIG. 4 is a flow chart illustrating a method for implementing guided meditation using the portable audio device according to the present disclosure.

FIG. 4 illustrates a flow chart illustrating operation of a portable audio device 100 according to the present disclosure. At 402, a user commences a guided mindfulness meditation session by activating a guided meditation session on the portable audio device 100. In one embodiment, the user may select a particular guided meditation session from the Guided Meditation Library 118 to be output during the session. The user may select a guided meditation session by accessing the Guided Meditation Library 118 via the input/output device 106 (such as touch screen display, user interface, selection buttons, etc.) to select a particular session. The user may select a guided meditation session with respect to, for example, a particular theme, author, subject matter, sound output, duration, and the like. In another embodiment, a guided meditation session may be randomly selected via the processor 102 and/or audio controller 114 using any suitable random selection mechanism known in the art.

In one embodiment, at 404, the user may select at least one audio output control parameter for controlling at least one operational parameter of the audio output of the guided meditation session. For example, the user may select a specified volume for the guided meditation session, a particular audio characteristic of sound emitted from the speaker component 112, a timing for the guided meditation session, and the like. Upon the user selecting at least one audio output control parameter, the processor 102 and/or audio controller 114 may generate at least one control signal for controlling the audio output of the guided meditation session.

At 406, the selected guided meditation session is commenced, and the content is output by the speaker component 112 in accordance with the at least one control signal. In one embodiment, prior to playing the selected guided meditation session, introductory content may be output by the speaker component 112 providing the user with information as to the purpose of the session, the content of the session, meditation practice tips, and the like.

During the guided meditation session, the user may listen to and/or participate in the session in any suitable manner as shown at 408. For example, the user may listen to the guided meditation session during restful periods, such as upon waking, prior to falling asleep at night, or any other suitable restful, meditative period during the day. As another example, the user may listen to the guided meditation session while undertaking other activities or common routines.

In one embodiment, upon completion of the guided meditation session, the portable audio device 100 may power off as shown at 410. In another embodiment, upon completion of the guided meditation session, the user may be presented with the option to continue the meditation process. If the user elects to continue with guided meditation, the process returns to step 402, wherein a guided meditation session is selected for playback.

Operational embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, a DVD disk, or any other form of storage medium known in the art. An exemplary storage medium is coupled to the processor such the processor may read information from, and write information to, the storage medium. In the alternative, the storage medium may be integral to the processor.

The processor and the storage medium may reside in an ASIC or may reside as discrete components in another device.

Furthermore, the one or more versions may be implemented as a method, apparatus, or article of manufacture using standard programming and/or engineering techniques to produce software, firmware, hardware, or any combination thereof to control a computer to implement the disclosed embodiments. Non-transitory computer readable media may include but are not limited to magnetic storage devices (e.g., hard disk, floppy disk, magnetic strips), optical disks (e.g., compact disk (CD), digital versatile disk (DVD)), smart cards, and flash memory devices (e.g., card, stick). Those skilled in the art will recognize many modifications may be made to this configuration without departing from the scope of the disclosed embodiments.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those of ordinary skill in the art that various modifications and variations may be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A portable audio device for facilitating guided meditation sessions comprising:
   a device processor operable for controlling the portable audio device;
   an input/output device operatively connected to the device processor and controlled in part by the device processor, wherein the input/output device is operable to transmit data to and from the device processor;
   an audio output component operatively coupled to the device processor and controlled in part by the device processor, wherein the audio output component is operable to output a plurality of sounds therefrom, wherein the audio output component comprises:
   an audio memory operable to store an audio library comprising a plurality of audio data files containing audio data for playback thereof; wherein the plurality of audio data files comprises a plurality of guided meditation programs, wherein the plurality of guided meditation programs include a plurality of guided meditation program modes;
   wherein the plurality of guided mediation program modes comprises a plurality of predefined theme modes, wherein each predefined theme mode comprises guided meditation programs containing content directed to the predefined theme;
   an audio controller operable to access audio data contained in at least one of the plurality of audio data files, wherein the audio controller is operable to generate, based on at least a portion of the accessed audio data, at least one audio output control signal for controlling the output of a guided meditation program; and
   a speaker component operatively coupled to the audio controller and controlled in part by the audio controller, wherein the speaker component is operable to output the guided meditation program in accordance with the at least one audio output control signal; and
   a power source operatively coupled to the device processor, wherein the power source is operable to generate a supply of power for operation of the portable audio device;
   wherein the device processor is operable to:
   obtain data associated with at least one operational parameter for an audio output of a guided meditation program by the audio output component;
   generate at least one device control signal for controlling the at least one operational parameter for the audio output of the guided meditation program; and
   transmitting the at least one device control signal to the audio output component for outputting the at least one guided meditation program in accordance with the at least one device control signal.

2. The portable audio device of claim 1, wherein the at least one operational parameter for an audio output of a guided meditation program by the audio output component is selected from the group consisting of a selection of at least one guided meditation program to be output, an audio characteristic of a guided meditation program to be output, a timing of a guided meditation program to be output, a duration of a guided meditation program to be output, and combinations thereof.

3. The portable audio device of claim 1, wherein the audio controller is operable to generate, based on at least a portion of the accessed audio data, at least one audio output control signal for controlling at least one of: a type of guided meditation program output from the audio output component, an audio characteristic of a guided meditation program emitted from the audio output component, a timing of a guided meditation program emitted from the audio output component, and combinations thereof.

4. The portable audio device of claim 1, wherein at least portion of the plurality of guided meditation programs have a duration of less than 10 minutes.

5. The portable audio device of claim 1, wherein the plurality of guided meditation program modes comprises a least a short duration program mode and a long duration program mode.

6. The portable audio device of claim 5, wherein the short duration program mode has a duration of approximately 2 minutes to approximately 5 minutes and wherein the long duration program mode has a duration of approximately 5 minutes to approximately 10 minutes.

7. The portable audio device of claim 1, wherein the predefined theme modes are selected from the group consisting of breath, heart, performance, body scan, and stress and anxiety.

8. The portable audio device of claim 1, wherein the input/output device is operable to receive a plurality of commands for controlling at least one operational parameter for an audio output of a guided meditation program by the audio output component.

9. The portable audio device of claim 8, wherein the input/output device further comprises a user interface, wherein at least a portion of the plurality of commands are received from an associated user via the user interface.

10. The portable audio device of claim 1, wherein the input/output device is operable to connect the device processor to an associated network for communication with a remote computing device, wherein the input/output device is operable to receive data from the remote computing device and transmit the received data to the device processor for processing thereof.

11. The portable audio device of claim 10, wherein the input/output device is operable to receive a plurality of commands from the remote computing device for controlling at least one operational parameter for an audio output of a guided meditation program by the audio output component.

12. A method for facilitating guided meditation sessions via a portable audio device, the portable audio device comprising (a) a device processor operable controlling the portable audio device, (b) an input/output device is operable to transmit data to and from the device processor, (c) an audio output component is operable to output a plurality of sounds therefrom, wherein the audio output component comprises (i) an audio memory operable to store an audio library comprising a plurality of audio data files containing audio data for playback thereof, wherein the plurality of audio data files comprise a plurality of guided meditation programs, wherein the plurality of guided meditation programs include a plurality of guided meditation program modes, wherein the plurality of guided meditation program modes comprises a plurality of predefined theme modes, wherein each predefined theme mode comprises guided meditation programs containing content directed to the predefined theme, (ii) an audio controller operable to access audio data contained in at least one of the plurality of audio data files, and (iii) a speaker component operable to output guided meditation programs; and (d) a power source operable to generate a supply of power for operation of the portable audio device, the method comprising:

receiving a command to activate the portable audio device;

obtaining data associated with at least one operational parameter for an audio output of a guided meditation program by the device processor;

generating, by the device processor, at least one device control signal for controlling the at least one operational parameter for the audio output of the guided meditation program;

transmitting, by the input/output device, the at least one device control signal to the audio controller;

accessing, by the audio controller, audio data contained in at least one of the plurality of audio data files in accordance with at least one device control signal;

generating, by the audio controller; based on at least a portion of the accessed audio data, at least one audio output control signal for controlling the output of a guided meditation program; and outputting, by the speaker component, the guided meditation program in accordance with the at least one audio output control signal.

13. The method of claim 12, wherein the at least one operational parameter for an audio output of a guided meditation program by the audio output component is selected from the group consisting of a selection of at least one guided meditation program to be output, an audio characteristic of a guided meditation program to be output, a timing of a guided meditation program to be output, a duration of a guided meditation program to be output, and combinations thereof.

14. The method of claim 12, wherein at least portion of the plurality of guided meditation programs have a duration of less than 10 minutes.

15. The method of claim 12, wherein the plurality of guided meditation program modes comprises a least a short duration program mode and a long duration program mode.

16. The method of claim 12, further comprising receiving, via the input/output device, a plurality of commands for controlling at least one operational parameter for an audio output of a guided meditation program by the audio output component.

17. The method of claim 12, further comprising receiving, via the input/output device, data from a remote computing device via an associated network and transmitting the received data to the device processor for processing thereof.

* * * * *